US006966336B1

(12) United States Patent
Renzi

(10) Patent No.: US 6,966,336 B1
(45) Date of Patent: Nov. 22, 2005

(54) FLUID INJECTION MICROVALVE

(75) Inventor: Ronald F. Renzi, Tracy, CA (US)

(73) Assignee: Sandia National Laboratories, Livermore, CA (US)

( * ) Notice: Subject to any disclaimer, the term of this patent is extended or adjusted under 35 U.S.C. 154(b) by 276 days.

(21) Appl. No.: 10/350,626

(22) Filed: Jan. 24, 2003

(51) Int. Cl.[7] .......................... F16K 11/074; G01N 1/20
(52) U.S. Cl. ................. 137/625.18; 73/863.73
(58) Field of Search ................. 137/625.18; 73/863.73; 251/170, 188, 192; 422/103

(56) References Cited

U.S. PATENT DOCUMENTS

| | | | | |
|---|---|---|---|---|
| 2,959,330 | A | * | 11/1960 | Charbonneau ......... 137/625.18 |
| 3,080,759 | A | * | 3/1963 | McQuaid .................. 73/863.73 |
| 3,677,577 | A | | 7/1972 | Krauer et al. ................ 285/137 |
| 3,693,661 | A | * | 9/1972 | Aurenge et al. ....... 137/625.18 |
| 3,885,439 | A | * | 5/1975 | Stone ........................ 73/863.73 |
| 4,085,618 | A | * | 4/1978 | Collins, Jr. ............... 73/863.73 |
| 4,089,549 | A | | 5/1978 | Vyse et al. ................... 285/137 |
| 4,346,610 | A | * | 8/1982 | Ishii et al. ................ 73/863.73 |
| 4,562,748 | A | * | 1/1986 | Mrochek et al. ......... 73/863.73 |
| 4,915,419 | A | | 4/1990 | Smith, III .................... 285/26 |
| 4,995,646 | A | | 2/1991 | Johnston et al. ............ 285/137 |
| 5,209,525 | A | | 5/1993 | Ito .............................. 285/137 |
| 5,295,400 | A | * | 3/1994 | Tatani et al. .............. 73/863.73 |
| 5,366,620 | A | | 11/1994 | Schick ........................ 210/198 |
| 5,419,208 | A | | 5/1995 | Schick ..................... 73/863.73 |
| 5,472,598 | A | | 12/1995 | Schick ........................ 210/198 |
| 5,482,628 | A | | 1/1996 | Schick ........................ 210/198 |
| 5,487,569 | A | | 1/1996 | Silvis et al. .................. 285/24 |
| 5,494,641 | A | | 2/1996 | Krstanovic .................. 422/103 |
| 5,534,152 | A | | 7/1996 | Schick ........................ 210/656 |
| 5,540,464 | A | | 7/1996 | Picha .......................... 285/328 |
| 5,644,395 | A | | 7/1997 | Folta .......................... 356/246 |
| 5,736,036 | A | | 4/1998 | Upchurch et al. .......... 210/198 |
| 5,842,680 | A | * | 12/1998 | Bustamante et al. ........ 251/192 |
| 5,846,396 | A | | 12/1998 | Zanzucchi et al. .......... 204/601 |
| 5,855,229 | A | | 1/1999 | Gulf, Jr. ...................... 137/884 |
| 5,865,474 | A | | 2/1999 | Takahashi ................. 285/124.1 |
| 5,987,735 | A | | 11/1999 | Horning et al. ............... 29/737 |
| 5,988,703 | A | | 11/1999 | Craig ....................... 285/288.1 |

(Continued)

OTHER PUBLICATIONS

U.S. Appl. No. 10/351,714, filed Jan. 27, 2003, Renzi.

(Continued)

Primary Examiner—John Rivell
(74) Attorney, Agent, or Firm—Cascio, Schmoyer & Zervas

(57) ABSTRACT

A microvalve for extracting small volume samples into analytical devices, e.g., high pressure liquid chromatography (HPLC) column, includes: a first body having a first interior surface and two or more outlet ports at the first interior surface that are in fluid communication with two or more first channels; a second body having a second interior surface and two or more inlet ports at the second interior surface that are in fluid communication with two or more second channels wherein the outlet ports of the first body are coaxial with the corresponding inlet ports of the second body such that there are at least two sets of coaxial port outlets and port inlets; a plate member, which has a substantially planar first mating surface and a substantially planar second mating surface, that is slidably positioned between the first interior surface and the second interior surface wherein the plate member has at least one aperture that traverses the height of the plate member, and wherein the aperture can be positioned to be coaxial with any of the at least two sets of coaxial port outlets and port inlets; and means for securing the first surface of the first body against the first mating surface and for securing the second surface of the second body against the second mating surface.

42 Claims, 2 Drawing Sheets

U.S. PATENT DOCUMENTS

| | | |
|---|---|---|
| 6,083,763 A | 7/2000 | Balch .......................... 436/518 |
| 6,086,825 A | 7/2000 | Sundberg et al. ........... 422/100 |
| 6,090,251 A | 7/2000 | Sundberg et al. ........... 204/453 |
| 6,102,449 A | 8/2000 | Welsh ......................... 285/342 |
| 6,102,987 A | 8/2000 | Gross et al. ................. 604/246 |
| 6,129,331 A | 10/2000 | Henning et al. .............. 251/11 |
| 6,190,616 B1 | 2/2001 | Jovanovich et al. ........ 422/103 |
| 6,224,728 B1 | 5/2001 | Oborny et al. .............. 204/450 |
| 6,267,143 B1 | 7/2001 | Schick .................. 137/625.11 |
| 6,293,725 B1 | 9/2001 | Winkvist .................... 403/282 |
| 6,312,960 B1 | 11/2001 | Balch et al. ................. 436/518 |
| 6,319,476 B1 | 11/2001 | Victor, Jr. et al. .......... 422/103 |
| 6,344,145 B1 | 2/2002 | Garguilo et al. ............ 210/635 |
| 6,358,387 B1 | 3/2002 | Kopf-Sill et al. ........... 204/603 |
| 2001/0045235 A1 | 11/2001 | Schick |

OTHER PUBLICATIONS

U.S. Appl. No. 10/350,541, filed Jan. 24, 2003, Renzi.
U.S. Appl. No. 10/405,204, filed Apr. 2, 2003, Renzi.
U.S. Appl. No. 10/405,842, filed Apr. 2, 2003, Renzi et al.
U.S. Appl. No. 10/350,628, filed Jan. 24, 2003, Renzi.

* cited by examiner

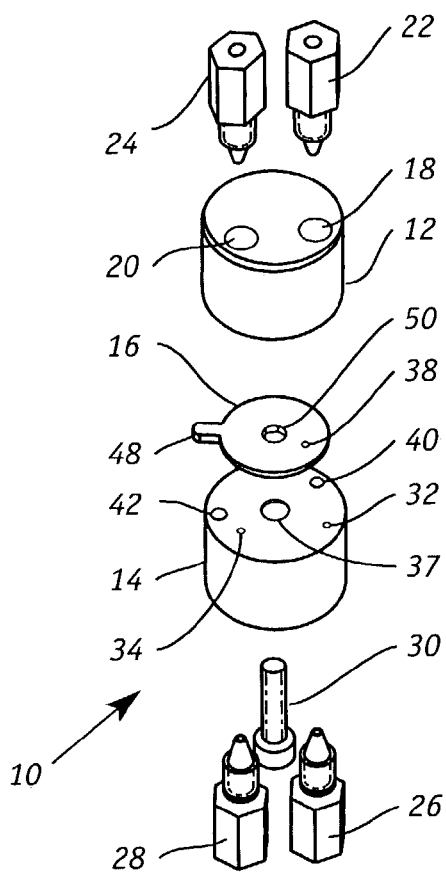
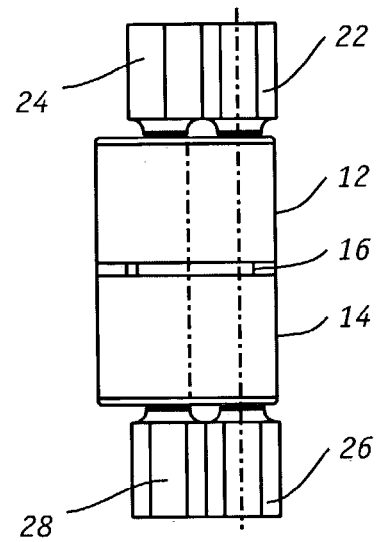
FIG. 2
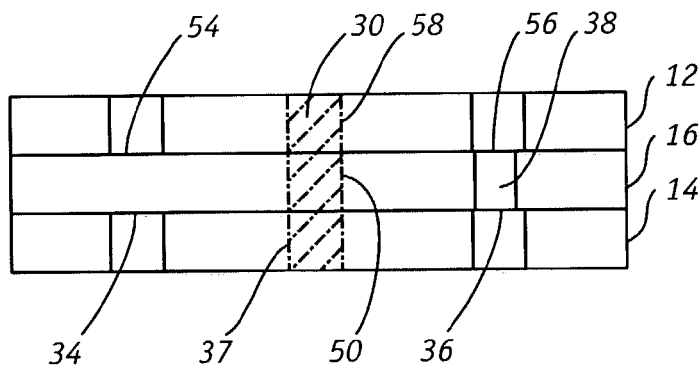
FIG. 1
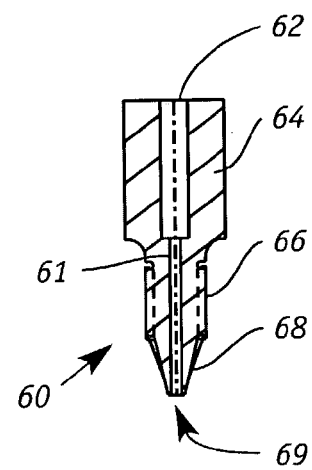
FIG. 3
FIG. 4

FLUID INJECTION MICROVALVE

This invention was made with Government support under Contract No. DE-AC04-94AL85000 awarded by the U.S. Department of Energy to Sandia Corporation. The Government has certain rights to the invention.

FIELD OF THE INVENTION

The present invention relates generally to microfluidic systems and more particularly to microvalves for injecting control fluid samples from one capillary stream into another capillary stream. The microvalves can be employed in high pressure liquid chromatography and other analytical techniques.

BACKGROUND OF THE INVENTION

Devices for performing chemical analysis have in recent years become miniaturized. For example, microfluidic devices have been constructed using microelectronic fabrication and micromachining techniques on planar substrates such as glass or silicon which incorporate a series of interconnected channels or conduits to perform a variety of chemical analysis such as capillary electrophoresis (CE) and high-performance liquid chromatography (HPLC).

Microfluidic substrates have networks of chambers connected by channels which have mesoscale dimensions, where at least one dimension is usually between 0.1 microns and 500 microns. Such microfluidic substrates may be fabricated using photolithographic techniques similar to those used in the semi-conductor industry, and the resulting devices can be used to perform a variety of sophisticated chemical and biological analytical techniques. Microfluidic analytical technology has a number of advantages, including the ability to use very small sample sizes, typically on the order of nanoliters. The substrates may be produced at a relatively low cost, and can be formatted to perform numerous specific analytical operations, including mixing, dispensing, valving, reactions, and detections.

Another recently developed class of sample-receiving microfluidic substrates includes substrates having a capillary interface that allows compounds to be brought onto the test substrate from an external source, and which can be advantageously used in a number of assay formats for high-throughput screening applications. These assay formats include fluorogenic assays, fluorescence polarization assays, non-fluorogenic mobility shift assays, dose response assays, and calcium flux cell-based assays.

Other applications for microfluidic devices include diagnostics involving biomolecules and other analytical techniques such as micro total analysis systems. Such devices, often referred to in the art as "microchips," also may be fabricated from plastic, with the channels being etched, machined or injection molded into individual substrates. Multiple substrates may be suitably arranged and laminated to construct a microchip of desired function and geometry. In all cases, the channels used to carry out the analysis typically are of capillary scale dimension.

To fully exploit the technological advances offered by the use of microfluidic devices and to maintain the degree of sensitivity for analytical techniques when processing small volumes, e.g., microliters or less, connectors which introduce and/or withdraw fluids, i.e., liquids and gases, from the device, as well as interconnect microfluidic devices, are a crucial component in the use and performance of the microfluidic device.

Specifically, it is critical for accurate analysis that precise amounts of samples be available especially when analyzing complex samples. This is difficult to achieve especially in high pressure applications such as microanalytical pressure-drive chromatography.

SUMMARY OF THE INVENTION

The invention is based in part on the development of a microvalve for extracting small volume samples into analytical devices, e.g., high pressure liquid chromatography (HPLC) column. In one aspect, the invention is directed to a microvalve that includes:

a first body having a first interior surface and two or more outlet ports at the first interior surface that are in fluid communication with two or more first channels;

a second body having a second interior surface and two or more inlet ports at the second interior surface that are in fluid communication with two or more second channels wherein the outlet ports of the first body are coaxial with the corresponding inlet ports of the second body such that there are at least two sets of coaxial port outlets and port inlets;

a plate member, which has a substantially planar first mating surface and a substantially planar second mating surface, that is slidably positioned between the first interior surface and the second interior surface wherein the plate member has at least one aperture that traverses the height of the plate member, and wherein the aperture can be positioned to be coaxial with any of the at least two sets of coaxial port outlets and port inlets; and means for securing the first surface of the first body against the first mating surface and for securing the second surface of the second body against the second mating surface.

In another aspect, the invention is directed to a method of extracting a measured amount of sample from a first fluid stream and introducing the extracted sample into a second fluid stream that includes the steps of:

(a) providing a microvalve that includes:
   (i) a first body having a first interior surface and two or more outlet ports at the first interior surface that are in fluid communication with two or more first channels;
   (ii) a second body having a second interior surface and two or more inlet ports at the second interior surface that are in fluid communication with two or more second channels wherein the outlet port of the first body are coaxial with the corresponding inlet ports of the second body such that there are at least two sets of coaxial port outlets and port inlets;
   (iii) a plate member, which has a substantially planar first mating surface and a substantially planar second mating surface, that is slidably positioned between the first interior surface and the second interior surface wherein the plate member has at least one aperture that traverses the height of the plate member, and wherein the aperture can be positioned to be coaxial with any of the at least two sets of coaxial port outlets and port inlets; and
   (iv) means for securing the first surface of the first body against the first mating surface and for securing the second surface of the second body against the second mating surface;

(b) connecting a first channel to a first outlet port of the first body;

(c) connecting a second channel to a second outlet port of the first body;

(d) connecting a third channel to a first inlet port of the second body;

(e) connecting a fourth channel to a second inlet port of the second body;

(f) maneuvering the aperture to a first position so that fluid flows from the first channel to the third channel through the aperture;

(g) maneuvering the aperture away from the first position so that a fluid sample is entrapped within the aperture; and (h) maneuvering the aperture to a second position so that the fluid sample flows into the second or fourth channel.

BRIEF DESCRIPTION OF THE DRAWINGS

FIG. 1 is a perspective view of one embodiment of the dissembled microvalve;

FIG. 2 is an elevational front view of an assembled microvalve;

FIG. 3 is a schematic partial cross sectional view of the microvalve;

FIG. 4 is cross sectional view of a ferrule;

DESCRIPTION OF THE PREFERRED EMBODIMENTS

Figure 5:
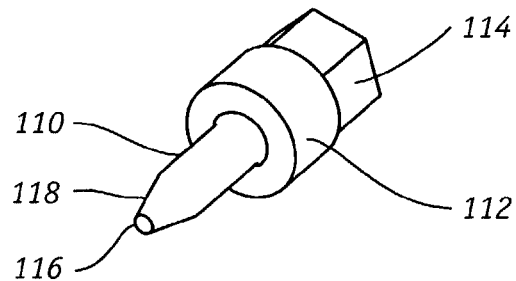
FIGS. 5 and 6 are perspective and cross sectional views of the ferrule.

This invention is directed to a microvalve for extracting small, e.g., 1–10 nL samples, and injecting the samples into a second fluid stream. The microvalve is particularly suited for introducing the extracted sample into an analysis device such as, for example, a high pressure liquid chromatography column. While the invention will be described with liquid samples, it is understood that the microvalve can be employed with gaseous fluids as well.

As illustrated in FIGS. 1 and 2, microvalve 10 includes a first body 12 and a second body 14 and a movable slide plate 16 situated between them. Each body is preferably fabricated of metal, ceramic, or polymer material such as, for example, polyether ether ketone, high density polyethylene, or polytetrafluoroethylene. The slide plate can also be fabricated of metal, ceramic, or polymer material.

First body 12 includes two threaded conical-shaped cavities 18 and 20 that are configured to receive threaded sealing ferrules 22 and 24, respectively. The first body 12 can include additional threaded conical-shaped cavities with accompanying ferrules, if desired. The end of each sealing ferrule that is inserted into the receiving cavity is preferably conical-shaped in order to provide a liquid-tight seal when the sealing ferrule is screwed into the cavity. As explained further herein, each sealing ferrule has an internal cavity that runs the length of the sealing ferrule and that accommodates a capillary tube. Capillary tubes can be detachably secured in both bodies by compression of the sealing ferrule. First body 12 further defines two inlet openings, described herein, on its mating surface that faces slide plate 16; the two openings are concentric with the internal cavities of ferrules 22 and 24. Preferred capillaries have circular inner diameters that range from 5 microns to 250 microns. Capillaries are available commercially from numerous sources including, for example, Polymicro Technologies LLC (Phoenix, Ariz.).

Second body 14 similarly includes two threaded conical-shaped cavities that traverse the height of the second body and that are designed to receive threaded sealing ferrules 26 and 28, respectively. The second body can include additional threaded conical-shaped cavities with accompanying ferrules, if desired. The number of cavities in the first body does not have to be the same as that in the second body. Second body 14 further defines outlet openings 32 and 34 on its mating surface that faces slide plate 16 and that are concentric with the internal cavities of ferrules 26 and 28, respectively. As described herein, the two inlet openings of the first body are aligned with the two outlet openings of the second body so as to provide fluid communication between opposed pairs of capillaries held in the ferrules.

As shown in conjunction with the schematic of FIG. 3, movable slide plate 16, which is interposed between bodies 12 and 14, includes a small hole 38 that traverses the height of the slide plate 16 which can be manually rotated using handle 48 projecting the edge as shown in FIG. 1. Handle 48 can also be maneuvered with a motor or other electronic device, and/or with a pneumatic device. Thus, by rotating the slide plate, hole 38 can be aligned with either (i) inlet opening 56 to outlet 36 opening (FIG. 3) or (ii) inlet opening 54 to outlet opening 34. To facilitate alignment or registration of the openings of the bodies to hole 38 of the slide plate, the mating surface of second body 14 has two projections 40, 42, shown in FIG. 1, thereon, e.g., dowel pins, that serves as stops that engage handle 48 of the slide plate 16 to denote when hole 38 is properly aligned. If there are more than two sets of openings on the mating surface of each first and second bodies, then registration of the slide plate hole to the additional outlet and inlet openings can be accomplished with markings on the sides of the slide plate and first and second bodies.

The microvalve components are secured tightly with a bolt or screw 30 which is inserted through hole 37 of second body 14, hole 50 of slide plate 16, and hole 58 in first body 12. The three holes are concentric. In this fashion, the mating surfaces of the first and second bodies and the upper and lower surfaces of slide plate 16 provide fluid-tight seals when compressive pressure is applied and maintained by the screw. To insure a good seal, the mating surfaces and slide plate surfaces must be planar and should be sufficiently polished. It has been demonstrated that by simply bolting the components of the microvalve together without the use of external seals, the microvalve can be subjected to pressures of at least 500 psi without fluid leakage. The term "external seal" refers to a device that joins two systems or elements in such a way as to prevent leakage. The components of the microvalve can be secured also by screws that can be optionally spring loaded and/or other mechanical compressive devices. Alternatively, energy activated devices such as, for example, a solenoid controlled clamp, can be employed to exert a higher compressive force. It is expected that using a power operated device or high pressure clamping device to holding the microvalve components together tightly, will permit the microvalve to operate at pressures of 10,000 psi or higher.

FIG. 4 shows a threaded ferrule 60 that is designed to be screwed into the conically-shaped cavities in first and second bodies 12, 14 of the microvalve as shown in FIG. 1. The ferrule includes an upper handle 64, an externally threaded middle portion 66, and a lower tapered end 68. Ferrule 60 also has internal bore 61 that runs the length of the ferrule from inlet 62 to outlet 69. Preferably, internal bore 61 is narrower at the tapered end (as compared to the upper handle) of the ferrule so that while a capillary tube can readily fit into the narrower portion of the bore, the wall of the bore at the tapered end will collapse against the capillary tube as compressive forces are created as the ferrule is screwed into the thread tapered cavities of the first and second bodies of the microvalve. This effectively creates a liquid tight seal and prevents the capillary tube from extruding during high pressure operations. Preferably each ferrule is constructed as a single, integral piece with no mating sleeve. They can be fabricated by machining a single block of deformable material such as PEEK.

When connecting capillaries, one end of the capillary is preferably inserted into bore 61 of ferrule 60 until the end of the capillary tube reaches outlet 69 of the ferrule or slightly beyond outlet 69. The other end of the capillary is connected to a source of buffer, sample, waste reservoir, or chromatography device as the case may be.

Figure 6:
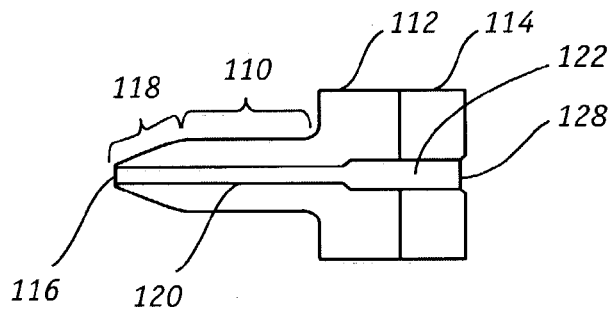

FIGS. 5 and 6 also depict a threaded, one piece ferrule that can also be screwed into a threaded conical-shaped cavity in the first and/or second bodies. The ferrule includes an adapter body 112 having an hexagonal nut 114 on one side and an elongated member 110,118 on the other side. End portion 118 of the elongated member is tapered. The ferrule has internal bore 120,122 that runs the length of the ferrule from inlet 128 to outlet 116. Preferably, as shown in FIG. 6, the proximal portion 122 of the bore is broader to facilitate insertion of a tube into the narrower distal portion 120 of the bore. The wall of the bore at the tapered end will collapse against the tube as compressive forces are created as the ferrule is screwed into the threaded conical-shaped cavity. This effectively creates a liquid tight seal and prevents the capillary tube from extruding during high pressure operations.

Each ferrule is machined from a block of material to fabricate a single, integral piece ferrule. A bore is formed using conventional drills and threads are machined preferably on the exterior of the non-taper portion 110 of the elongated member. When using the ferrule, no flange is needed. In addition, a mating sleeve is not needed since the bore will collapse directly against the tube under compressive force. By "mating sleeve" is meant an extra tube that is inserted into the bore of the ferrule before the capillary tube that will be transferring a fluid of interest is inserted through the bore of the mating sleeve. Mating sleeves having an outer diameter that matches the inner diameter of prior art ferrules are used quite often but are not needed with the inventive ferrule. Machining also permits exact tolerance to be maintained to improve fittings function. Because the inventive ferrules is fabricated by machining, that is, it is not made by molding, a wide range of materials, including plastics, ceramics, and metals, for example, can be used depending on the expected operating conditions, e.g., temperature, pressure, and type of fluids the ferrule will be exposed to. The ferrules are reusable and can be finger-tightened to provide a seal that can withstand a minimum pressure of 5,000 psi.

The ferrule is particularly suited for high pressure operations to connect capillary tubes for microfluidic applications. In this regard, referring to the ferrule shown in FIG. 6, the diameter of the distal portion 120 of the bore is preferably 0.0145 in. (0.368 mm) to 0.015 in. (0.38 mm) and the diameter of the proximal portion 122 of the bore is typically 0.018 in. (0.46 mm) to 0.020 in. (0.51 mm). In practice, one or more ferrule(s) each with a capillary tube is screwed into the appropriate threaded concical-shaped cavity. As the ferrule is screwed on, the compressive pressure causes the internal bore of the ferrule to collapse against the capillary tube thereby gripping the capillary and forming a fluid tight seal.

Figure 7:
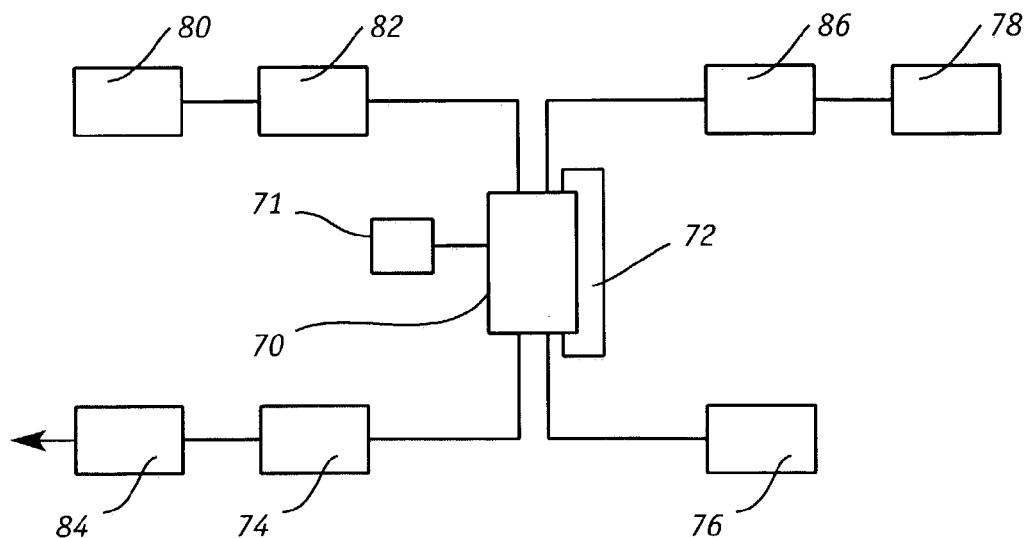
FIG. 7 is a schematic of a sample analysis system.

The microvalve is particularly suited for extracting small and carefully controlled sample volumes from a fluid stream and injecting the extracted sample volumes into analysis means such as a chromatographic column of a sample analysis system as illustrated in a FIG. 7. The system includes a microvalve 70, that is secured by a mechanical or motorized clamp 72, along with a source of sample for analysis 78, a source of buffer 80, and a waste reservoir 76, capillary electrophoresis column 74 and detector 84. Pumps 82 and 86 are employed to deliver buffer and sample, respectively, to microvalve 70. The inlet and outlet ports of the microvalve device 70 are connected to the other components of the sample analysis by capillaries which are commercially available. Motor 71 is employed to move handle 48 (FIG. 1). Alternatively, slide plate 16 (FIG. 1) can be maneuvered by other means, such as, with gear driven teeth on the other diameter of the slide plate.

Conventional mechanical pumps can be employed although a preferred method employs a high pressure hydraulic system that has no moving parts for converting electric potential to hydraulic force and for manipulating fluids which are described in U.S. Pat. No. 6,013,164 to Paul, et al., U.S. Pat. No. 6,019,882 to Paul, et al., U.S. Pat. No. 6,224,728 to Oborny, et al., and U.S. Pat. Nos. 6,277, 257 and 6,290,909 both to Paul, et al., which are all incorporated herein by reference.

For microfluidic operations involving sample volumes in the range of 1–10 nL, the capillaries have inner diameters in the range of 0.1 microns to 500 microns, and preferably less than 100 microns. The capillary is typically made of glass, metal, silica, or a polymer.

In operation, as shown in FIG. 3 slide plate 16 of the microvalve is positioned at a first position so that the sample from the source flows through one set of opposed capillaries through the slide plate hole 38 interposed therebetween and into waste reservoir. At an appropriate time, slide plate 16 and the portion of sample entrained in hole 38, is moved to a second position such that hole 38 is aligned with a second set of capillaries. Flowing a buffer solution through the second set of capillaries carries the sample entrained in slide plate hole 38 downstream for analysis. The volume of the slide plate hole, i.e., the diameter of the hole and the thickness of the slide plate, determine the quantity of sample analyzed. Changing the diameter of the slide plate hole and/or the thickness of the slide plate itself will change the volume of sample being analyzed.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. A microvalve that comprises:
a first body having a first interior surface and two or more outlet ports at the first interior surface that are in fluid communication with two or more first channels that each defines a threaded conical-shaped cavity and wherein at least one of the first channels has a first ferrule secured thereto wherein each first ferrule is externally threaded and defines a bore extending therethrough with each first ferrule supporting a first fluid conduit wherein each first ferrule is threaded into the channel of the first body and wherein each first ferrule defines a lower tapered exterior end;

a second body having a second interior surface and two or more inlet ports at the second interior surface that are in fluid communication with two or more second channels wherein the outlet ports of the first body are coaxial with the corresponding inlet ports of the second body such that there are at least two sets of coaxial port outlets and port inlets that each defines a threaded conical-shaped cavity and wherein at least one of the second channels has a second ferrule secured thereto wherein each second ferrule is externally threaded and defines a bore extending therethrough with each second ferrule supporting a second fluid conduit wherein each second ferrule is threaded into the channel of the second body and wherein each second ferrule defines a lower tapered exterior end;

a plate member, which has a substantially planar first mating surface and a substantially planar second mating surface, that is slidably positioned between the first interior surface and the second interior surface wherein the plate member has at least one aperture that traverses the height of the plate member, and wherein the aperture can be positioned to be coaxial with any of the at least two sets of coaxial port outlets and port inlets; and means for securing the first surface of the first body against the first mating surface and for securing the second surface of the second body against the second mating surface that enables the microvalve to operate at a pressure of at least 500 psi without fluid leakage.

2. The microvalve of claim 1 wherein said securing means comprises a power operated device that generates a compressive force.

3. The microvalve of claim 1 wherein said securing means is selected from the group consisting of a bolt, screw, screw with spring clamps, electrically activated solenoid, and combinations thereof.

4. The microvalve of claim 1 wherein each of the first body and second body is made of a polymer that is selected from the group consisting of polyether ether ketone, high density polyethylene, and polytetrafluoroethylene.

5. The microvalve of claim 1 wherein each of the first body and second body is made of material that is selected from the group consisting of metal, ceramic, and polymer.

6. The microvalve of claim 1 wherein the first body includes two or more first bores each of which secures a first ferrule that has a cavity that holds a first capillary and the second body includes two or more second bores each of which secures a second ferrule that has a cavity that holds a second capillary.

7. The microvalve of claim 1 wherein each of the at least one aperture defines a volume of from about 1 nL to 10 nL.

8. The microvalve of claim 1 wherein the first body defines a first hole, the second body defines a second hole, and the plate member defines third hole, wherein the first hole, second hole, and third hole are concentric and accommodate said securing means.

9. The microvalve of claim 8 wherein said securing means is selected from the group consisting of a bolt, screw, screw with spring, electrically activated solenoid, and combinations thereof.

10. The microvalve of claim 1 further including means for registering the aperture so as to be aligned with an outlet port and an inlet port.

11. The microvalve of claim 1 wherein external seals are not employed around any of the two or more port inlets or any of the two or more port outlets.

12. The microvalve of claim 1 wherein each of the first interior surface, second interior surface, first mating surface, and second mating surface is highly polished.

13. The microvalve of claim 1 wherein each ferrule is made of a deformable material.

14. The microvalve of claim 1 wherein a portion of each ferrule is sufficiently compressed against a part of a fluid conduit to form a fluid tight seal.

15. The microvalve of claim 14 wherein each ferrule comprises an adapter body having a nut on one side and having an elongated member on the other side and wherein the bore extends through the adapter body, nut and elongated member.

16. The microvalve of claim 15 wherein the lower tapered exterior end is on the elongated member.

17. The microvalve of claim 15 wherein the part of the bore that extends through the nut has a diameter that is larger than the part of the bore that extends through the elongated member.

18. The microvalve of claim 16 wherein each ferrule is an integral structure with no mating sleeve.

19. The microvalve of claim 1 wherein each ferrule comprises an upper handle, an externally threaded portion, and wherein the bore extends through the upper handle, externally threaded portion, and the lower tapered exterior end.

20. The microvalve of claim 19 wherein the part of the bore that extends through the tapered end has a diameter that is narrower than the part of the bore that extends through the handle.

21. The microvalve of claim 19 wherein each ferrule is an integral structure with no mating sleeve.

22. A method of extracting a measured amount of sample from a first fluid stream and introducing the extracted sample into a second fluid stream that comprises the steps of:

(a) providing a microvalve that comprises:

(i) a first body having a first interior surface and two or more outlet ports at the first interior surface that are in fluid communication with two or more first channels that each defines a threaded conical-shaped cavity and wherein at least two of the first channels each has a ferrule secured thereto wherein each ferrule is externally threaded and defines a bore extending therethrough with each ferrule supporting a first fluid conduit wherein each ferrule is threaded into the channel of the first body and wherein each ferrule defines a lower tapered exterior end;

(ii) a second body having a second interior surface and two or more inlet ports at the second interior surface that are in fluid communication with two or more second channels wherein the outlet port of the first body are coaxial with the corresponding inlet ports of the second body such that there are at least two sets of coaxial port outlets and port inlet wherein at least two of the second channels each defines a threaded conical-shaped cavity and has a ferrule secured thereto wherein each ferrule is externally threaded and defines a bore extending therethrough with each ferrule supporting a second fluid conduit wherein each ferrule is threaded into the channel of the second body and wherein each ferrule defines a lower tapered exterior end;

(iii) a plate member, which has a substantially planar first mating surface and a substantially planar second mating surface, that is slidably positioned between the first interior surface and the second interior surface wherein the plate member has at least one aperture that traverses the height of the plate member, and wherein the aperture can be positioned to be coaxial with any of the at least two sets of coaxial port outlets and port inlets; and (iv) means for securing the first surface of the first body against the first mating surface and for securing the second surface of the second body against the second mating surface that enables the microvalve to operate at a pressure of at least 500 psi without fluid leakage;

(b) maneuvering the aperture to a first position so that fluid flows from a first fluid conduit in the first body to a second fluid conduit in the second body through the aperture and a sample of fluid remains in the aperture; and (c) maneuvering the aperture to a second position so that the sample of fluid flows from the aperture into a third fluid conduit in the first body or a fourth fluid conduit in the second body.

23. The method of claim 22 wherein said securing means comprises a power operated device that generates a compressive force.

24. The method of claim 22 wherein said securing means is selected from the group consisting of a bolt, screw, screw with spring clamps, electrically activated solenoid, and combinations thereof.

25. The method of claim 22 wherein each of the first body and second body is made of a polymer that is selected from the group consisting of polyether ether ketone, high density polyethylene, and polytetrafluoroethylene.

26. The method of claim 22 wherein each of the first body and second body is made of material that is selected from the group consisting of metal, ceramic, and polymer.

27. The method of claim 22 wherein the first body includes two or more first bores each of which secures a first ferrule that has a cavity that holds a first capillary and the second body includes two or more second bores each of which secures a second ferrule that has a cavity that holds a second capillary.

28. The method of claim 22 wherein each of the at least one aperture defines a volume of from about 1 nL to 10 nL.

29. The method of claim 22 wherein the first body defines a first hole, the second body defines a second hole, and the plate member defines third hole, wherein the first hole, second hole, and third hole are concentric and accommodate said securing means.

30. The method of claim 29 wherein said securing means is selected from the group consisting of a bolt, spring loaded bolt, screw, spring loaded screw clamp, electrically activated solenoid and combinations thereof.

31. The method of claim 22 further including means for registering the aperture so as to be aligned with an inlet port and an outlet port.

32. The method of claim 22 wherein external seals art not employed around any of the two or more port outlets or any of the two or more port inlets.

33. The method of claim 22 wherein each of the first interior surface, second interior surface, first mating surface, and second mating surface is highly polished.

34. The method of claim 22 wherein each ferrule is made of a deformable material.

35. The method of claim 22 wherein a portion of each ferrule is sufficiently compressed against a part of a fluid conduit to form a fluid tight seal.

36. The method of claim 35 wherein each ferrule comprises an adapter body having a nut on one side and having an elongated member on the other side and wherein the bore extends through the adapter body, nut and elongated member.

37. The method of claim 36 wherein the lower tapered exterior end is on the elongated member.

38. The method of claim 36 wherein the part of the bore that extends through the nut has a diameter that is larger than the part of the bore that extends through the elongated member.

39. The method of claim 37 wherein each ferrule is an integral structure with no mating sleeve.

40. The method of claim 22 wherein each ferrule comprises an upper handle, an externally threaded portion, and wherein the bore extends through the upper handle, externally threaded portion, and the lower tapered exterior end.

41. The method of claim 40 wherein the part of the bore that extends through the tapered end has a diameter that is narrower than the part of the bore that extends through the handle.

42. The method of claim 40 wherein each ferrule is an integral structure with no mating sleeve.

* * * * *